(12) United States Patent
Harris et al.

(10) Patent No.: US 11,280,738 B2
(45) Date of Patent: Mar. 22, 2022

(54) METHOD AND APPARATUS FOR USE IN DIAGNOSIS AND MONITORING OF COLORECTAL CANCER

(71) Applicant: Swansea University, Swansea (GB)

(72) Inventors: Dean Harris, Pontyclun (GB); Peter Dunstan, Swansea (GB); Cerys Jenkins, Swansea (GB)

(73) Assignee: Swansea University, Swansea (GB)

( * ) Notice: Subject to any disclaimer, the term of this patent is extended or adjusted under 35 U.S.C. 154(b) by 0 days.

(21) Appl. No.: 16/494,428

(22) PCT Filed: Mar. 13, 2018

(86) PCT No.: PCT/GB2018/050627
§ 371 (c)(1),
(2) Date: Sep. 16, 2019

(87) PCT Pub. No.: WO2018/167470
PCT Pub. Date: Sep. 20, 2018

(65) Prior Publication Data
US 2020/0088646 A1    Mar. 19, 2020

(30) Foreign Application Priority Data
Mar. 15, 2017 (GB) .................................... 1704128

(51) Int. Cl.
*G01N 21/65* (2006.01)
*G01N 33/49* (2006.01)

(52) U.S. Cl.
CPC ............ *G01N 21/65* (2013.01); *G01N 33/49* (2013.01)

(58) Field of Classification Search
CPC .. G01N 21/65; G01N 33/49; G01N 33/57419; G01N 2500/10; G01N 2333/47; G01N 2333/70503; G01N 33/56977; G01N 21/658; G01N 2021/656; G01N 33/574; G01N 21/64; G01N 21/6458; G01N 21/35; G01N 2800/50; C12Q 1/6886; C12N 2502/11; G01J 3/44; G01J 3/0208; A61B 5/0075; A61B 5/0071
See application file for complete search history.

(56) References Cited

U.S. PATENT DOCUMENTS 8,810,789 B2 * 8/2014 Zhao ...................... G01N 21/65
356/301
8,846,331 B2 * 9/2014 McNaughton ... G01N 33/54326
435/29
(Continued)

FOREIGN PATENT DOCUMENTS

| CN | 103543139 B | 10/2015 |
|---|---|---|
| WO | WO 2012/153326 A1 | 11/2012 |
| WO | WO 2014/074569 A1 | 5/2014 |

OTHER PUBLICATIONS

Feng et al., "Label-free surface-enhanced Raman spectroscopy for detection of colorectal cancer and precursor lesions using blood plasma," *Biomed Opt. Express* 6:3494-3502, 2015.
(Continued)

*Primary Examiner* — Mohamed K Amara
(74) *Attorney, Agent, or Firm* — Klarquist Sparkman, LLP

(57) ABSTRACT

This invention relates to a method and apparatus for the early detection and monitoring of colorectal cancer via the sampling of a patient's blood.

22 Claims, 17 Drawing Sheets

(56) References Cited

U.S. PATENT DOCUMENTS

| | | | | |
|---|---|---|---|---|
| 8,918,161 | B2* | 12/2014 | Natan | C25D 1/006 600/431 |
| 9,964,492 | B2* | 5/2018 | Ito | G01N 21/658 |
| 10,215,700 | B2* | 2/2019 | Hasegawa | G01N 33/49 |
| 11,150,191 | B2* | 10/2021 | Weng | G01N 21/0303 |
| 2005/0211159 | A1* | 9/2005 | Meguro | C30B 25/18 117/68 |
| 2006/0084181 | A1* | 4/2006 | Farquharson | G01N 21/658 436/171 |
| 2006/0119853 | A1* | 6/2006 | Baumberg | G01N 21/658 356/445 |
| 2006/0253261 | A1* | 11/2006 | Maier | G01N 21/65 702/19 |
| 2007/0088219 | A1* | 4/2007 | Xie | G01N 21/65 600/473 |
| 2008/0003576 | A1* | 1/2008 | Zhang | C12Q 1/6816 435/6.11 |
| 2009/0046284 | A1* | 2/2009 | Wang | G01J 3/44 356/301 |
| 2010/0114514 | A1* | 5/2010 | Wang | G01J 3/0264 702/82 |
| 2011/0080581 | A1* | 4/2011 | Bhargava | G01J 3/0289 356/302 |
| 2011/0230760 | A1* | 9/2011 | Gambhir | A61K 49/0002 600/431 |
| 2011/0275061 | A1* | 11/2011 | Weidemaier | G01N 33/54333 435/6.1 |
| 2012/0092663 | A1* | 4/2012 | Kull | G01N 21/65 356/301 |
| 2013/0017298 | A1* | 1/2013 | Wang | G01N 21/65 426/231 |
| 2013/0115717 | A1* | 5/2013 | Guo | B82Y 30/00 436/501 |
| 2013/0131701 | A1* | 5/2013 | Komlos | A61L 31/047 606/151 |
| 2014/0333723 | A1* | 11/2014 | Dowaki | G01N 21/65 348/46 |
| 2014/0350534 | A1* | 11/2014 | Kircher | A61B 18/203 606/10 |
| 2015/0018807 | A1* | 1/2015 | Kircher | A61B 18/12 606/12 |
| 2015/0294076 | A1* | 10/2015 | Treado | G01N 33/57419 506/12 |
| 2015/0314013 | A1* | 11/2015 | Wickline | A61P 43/00 424/491 |
| 2016/0061808 | A1* | 3/2016 | Cheung | G01N 1/08 600/476 |
| 2016/0116334 | A1* | 4/2016 | Yang | G01N 21/658 356/301 |
| 2016/0187344 | A1* | 6/2016 | Ito | G01N 21/658 436/501 |
| 2016/0279214 | A1* | 9/2016 | Mahr | A61P 35/02 |
| 2017/0115216 | A1* | 4/2017 | Hasegawa | G01N 21/658 |
| 2018/0348136 | A1* | 12/2018 | Treado | G01J 3/44 |
| 2018/0372710 | A1* | 12/2018 | Lyng | G01N 21/3563 |

OTHER PUBLICATIONS

Digilab Identity-F Raman Reader brochure, retrieved from the internet: URL:http://www.accela.eu/files/products/117/digilab-identity-f-raman-reader-brochure.pdf, retrieved on Apr. 23, 2018.

InVia Raman microscopes brochure, retrieved from the internet: URL:https://www.labindia.com/labindia_instrument/nbp-pdf/brochure.pdf, retrieved on Apr. 23, 2018.

Jenkins et al., "Role of Raman spectroscopy and surface enhanced Raman spectroscopy in colorectal cancer," *World J Gastrointest Oncol.* 8:427-438, 2016.

Li et al., "Detection of colon cancer by laser induced Fluorescence and Raman spectroscopy," Proceedings of the 2005 IEEE, Engineering in Medicine and Biology 27$^{th}$ Annual Conference, pp. 6961-6964, Shanghai, China, Sep. 1-4, 2005.

Li et al., "Discrimination of serum Raman spectroscopy between normal and colorectal cancer," *Clinical and Biomedical Spectroscopy and Imaging II 8087*:1-5, 2011.

Li et al., "Discrimination of serum Raman spectroscopy between normal and colorectal cancer using selected parameters and regression-discriminant analysis," *Appl Optics 51*:5038-5043, 2012.

Li et al., "Discrimination of rectal cancer through human serum using surface-enhanced Raman spectroscopy," *Appl Phys. B 119*:393-398, 2015.

Lin et al., "Colorectal cancer detection by gold nanoparticle based surface-enhanced Raman spectroscopy of blood serum and statistical analysis," *Optics Express 19*:13565-13577, 2011.

Lin et al., "Diagnostic potential of polarized surface enhanced Raman spectroscopy technology for colorectal cancer detection," *Optics Express 24*:2222-2233, 2016.

Synytsya et al., "Raman spectroscopy at different excitation wavelengths (1064, 785 and 532 nm) as a tool for diagnosis of colon cancer," *J. Raman Spectrosc.* 45:903-911, 2014.

Wang et al., "Label-free detection of serum proteins using surface-enhanced Raman spectroscopy for colorectal cancer screening," *J Biomed. Optics 19*:087003, 2014.

Wang et al., "Blood test using surface-enhanced Raman spectroscopy with colloidal silver nanoparticle substrate to detect polyps and colorectal cancer," Conference Presentation, Progress in Biomedical Optics and Imaging, SPIE—International Society for Optical Engineering, Bellingham, WA, vol. 9704, p. 97040A, Mar. 7, 2016.

Great Britain Search Report for GB 1704128.6, dated Jun. 23, 2017 (4 pages).

International Search Report and Written Opinion for PCT/GB2018/050627, dated May 8, 2018 (18 pages).

* cited by examiner

METHOD AND APPARATUS FOR USE IN DIAGNOSIS AND MONITORING OF COLORECTAL CANCER

CROSS REFERENCE TO RELATED APPLICATIONS

This is the U.S. National Stage of International Application No. PCT/GB2018/050627 filed Mar. 13, 2018, which was published in English under PCT Article 21(2), which in turn claims the benefit of Great Britain Application No. 1704128.6, filed Mar. 15, 2017. The provisional application is incorporated herein in its entirety.

FIELD OF THE INVENTION

This invention relates to a method and apparatus for the early detection and monitoring of colorectal cancer via the sampling of a patient's blood.

BACKGROUND OF THE INVENTION

Bowel cancer is the third most common cancer and the second most common cause of cancer death in the UK, with around 38,000 new cases and 16,200 people dying each year. Patients continue to present at an advanced stage (55% stage III/IV) and often as an emergency (24%) with associated worse survival. The best patient outcomes are achieved when the disease is detected early and before symptoms arise. Despite bowel cancer screening programmes existing, public acceptance of current testing procedures has been poor. This may be attributed to the current testing method which requires a patient to post a faecal sample for laboratory testing for occult blood. Patients find this unpleasant and uptake has been found to be lower than expected at 55% through recent monitoring. An alternative recently piloted sigmoidoscopy screening programme found an even lower uptake.

A further problem is that even if blood is detected in faeces then it is not certain that a patient has colon cancer. Therefore, a further invasive test called a colonoscopy is required. The colonoscopy investigation is not without dangers such as the complication of bowel perforations. Typically, this colonoscopy test shows that about one in ten of all patients having the second test actually have cancer, with the rest (90%) having undergone a costly procedure (which has risk, takes significant time including the stress of the waiting time and requires surgical expertise) to find that they do not have cancer. Therefore, current screening methods are invasive, have initially low specificity for cancer and do not have widespread patient acceptance or uptake. These factors are propagating the number of advanced stage and emergency case referrals.

As such there is a pressing need to develop alternative non-invasive acceptable methods of screening for bowel cancer. The invention detailed here is a key pathway to producing a rapid diagnostic test that will help with initial patient triage and determine on-going treatment pathways, whilst also allowing for earlier detection. There are considerable cost savings to the health authority and/or patient due to the likely reduction in the need for endoscopy procedures, and a hence a more rapid approach to diagnostics without need for secondary care referral. The invention may also represent a means of detecting early recurrence of bowel cancer after treatment permitting earlier access to chemotherapy. The blood test may also define those patients who experience a 'complete response' to upfront combination chemo/radiotherapy for rectal cancer who could be spared radical surgery. This may be as many as 1 in 5 patients treated in such a way.

STATEMENT OF INVENTION

According to a first aspect of the present invention there is a method of determining an indication of the presence of colorectal cancer in a subject comprising the steps of:
performing laser spectroscopy on a blood or blood derivative sample obtained from the subject in order to obtain at least one output spectrum;
comparing the output spectrum to a control dataset comprising a plurality of known output spectra, where the plurality of known output spectra are derived from the blood or blood derivative samples of a plurality of first subjects having colorectal cancer and plurality of second subjects not having colorectal cancer; and
from the comparison determining whether the subject has an indication of the presence of colorectal cancer.

The determination of whether the subject has colorectal cancer may for example be a difference in the output spectrum and the control dataset or a match between the output spectrum and the control dataset. The method outputs an indication of the presence or not of colorectal cancer. The output may also indicate whether further investigation is required by a medical practitioner.

Spectroscopy is able to produce a chemical fingerprint of a sample and hence identify unique features in the serum sample when compared to others by measuring the scattered radiation intensity as a function of wavenumber (an energy scale used to show the shift in energy of the scattered light).

The invention enables identification within a subject's blood of the contributions that exist due to a patient exhibiting colorectal cancer. This means that the existing requirements for laboratory testing of faecal matter for blood, which if present is then followed up by performing colonoscopy to determine whether the presence of the blood is indicative of colorectal cancer, may no longer be required for many subjects or indeed be the best route for diagnosis. Detection or progression of colorectal cancer can be determined via a comparatively simple test. The test is based upon testing serum from a patient's blood sample, thus is both quick and relatively non-invasively. Detection at a much earlier stage can potentially be made and, through improvements in sensitivity/specificity, the follow up treatments (e.g. colonoscopy with progression to colectomy and chemotherapy) would be targeted more effectively, hence increasing life expectancy and massively reducing the cost burden. Accordingly, a colorectal cancer diagnostic capability has been developed with high sensitivity and specificity. Furthermore, progress of the cancer and the potential effect of treatment can be monitored through ongoing comparisons of the subject against the original cancer-indicative spectrum or spectra taken from a subject.

The laser spectroscopy technique is preferably Raman spectroscopy as it is non-destructive and can be applied robustly to liquid samples, as water creates minimal interference to successful analysis.

The blood sample can be obtained from a patient by any commonly known blood extraction method. The blood may be subjected to laser spectroscopy, or alternatively the blood may be separated. Thus, spectroscopy may be carried out upon a blood derivative such as serum or plasma. These blood derivatives or components may be separated from the blood by known techniques. Serum is preferred for increased sensitivity.

The output spectrum is preferably recorded across one or more wavenumbers, or one or more ranges of wavenumbers. An increase or decrease in peak intensity at the same wavenumber or a shift in position of the peak intensity between wavenumbers and/or a variation in the peak lineshape obtained between the blood or blood derivative sample and the control dataset may be indicative of a subject suffering from colorectal cancer. Key changes are compared to spectra taken from cancer and non-cancer controls. Peak line-shape means the shape of the plotted spectra and may for example relate to the gradient of the line before or after the peak, or the emergence of additional peak components due to a changing composition.

In Raman spectroscopy the reproducibility of spectra is also subject to sampling protocols and the types of analysis employed. The unique combination of analysis, use of controls and sampling methodology that are detailed here have revealed a colorectal cancer diagnostic capability with high sensitivity and specificity. The invention detailed describes both dried and liquid sampling processes and also the potential for high throughput analysis.

The control dataset comprises spectra from first subjects having colorectal cancer and second subjects not having colorectal cancer. The comparison is preferably made against a library of first subjects having colorectal cancer and second subjects not having colorectal cancer.

A plurality of subject spectra are preferably obtained by the laser spectroscopy for use in the comparison. A suitable number may, for example, be five spectra.

The blood or blood derivative sample obtained from the subject is preferably in liquid form. This minimises additional drying processes. The blood or blood derivative sample is preferably fresh.

The liquid form methodology involves performing spectroscopy on the first liquid sample wherein the blood or blood derivative sample from the subject is provided in a well in a sample holder. The well may be defined by a metal wall, wherein the metal may be stainless steel or aluminium. Advantageously, it has been found that the use of a metal well for sample holding minimises any interference when taking spectra readings of the sample, thereby improving sensitivity and reproducibility and providing a viable sample holder for Raman analysis. The well is preferably circular. The well depth may be between 4 mm and 8 mm, even more preferably between 5 mm and 7 mm, and even more preferably substantially 6 mm. The well diameter is preferably between 5 mm and 9 mm, even more preferably between 6 mm and 8 mm, and even more preferably substantially 7 mm. It has been found that when using these well dimensions, there is minimal masking of spectral readings from the sample, with dimensions outside these parameters showing greater cross-sample variation and therefore reduced reproducibility. The aim of the invention is to accurately discriminate between cancer and non-cancer in a sample, and therefore reproducibility and reliability is paramount.

For high throughput sampling the well is preferably defined in a sample holder, where there is a plurality of wells defined in the sample holder. In such an arrangement there may be a cooling arrangement, preferably comprising a cooling plate, for cooling and optimally maintaining a fixed temperature of both the sample holder (and thus the contained first sample).

The light source of the spectrometer is preferably focussed at between 1.1 and 1.3 mm above the bottom of the well, and even more preferably at approximately 1.2 mm above the bottom of the well. The bottom of the well is the lowermost point at which blood or blood derivative can locate in the well. It has been found that spectra readings are influenced by laser focus upon the sample, with non-optimised focus leading to a masking of background signatures that reduces reliability of spectra output. It has been advantageously found that focus depth as defined represents an optimum focus when considering the spectra regions of interest in analysis, with reduced background variability and improved discrimination.

The sample may also be analysed once dried. The method may comprise the step of drying the sample. The drying step may involve drying the first sample at room temperature or via assisted drying (e.g. vacuum drying). It is beneficial that the sample may be dried on the sample holder. The sample holder may be metallic and is preferably formed of aluminium. The sample holder is beneficially non-reusable.

In a further preferred embodiment, the sample to be analysed is cooled. By doing this, it has been found that there is less variability in spectra readings and hence better discrimination. In yet a further preferred embodiment, the sample is cooled to a temperature within the range 4° C. to 25° C., including every 0.1° C. therebetween. More preferably, said sample is cooled to a temperature within the range 10° C. to 20° C. including every 0.1° C. therebetween. Yet more preferably still said sample is cooled to a temperature within the range 15° C. to 20° C.

The light source is preferably a laser light source. The laser spectroscopy preferably subjects the sample to a first and second, different, wavelength of light to obtain a first and second spectrum, where the comparison step uses the first and second spectrum in the comparison. This provides a cross validation to the determination of the presence of colorectal cancer. For example, if a subject is taking medication, suffering from an unrelated illness or has previously suffered from cancer, this may have an unintended influence on the spectrum obtained. Using a first and a second different wavelength of light to obtain a first and second spectrum promotes different responses from the sample enabling validation of the spectra obtained. The first and second wavelength of light are preferably administered sequentially to the sample.

The first wavelength may be in the wavelength band of visible light, and the second wavelength may be in the wavelength band of infrared light, where the respective wavelengths may be about 532 nm and about 785 nm, respectively.

The output spectrum is preferably recorded between 610 cm$^{-1}$ and 1718 cm$^{-1}$. This range has been determined to encompass the fullest spectral output that allows reproducible discrimination.

The, or each, spectra preferably undergoes a processing step prior to the comparison step to reduce the noise associated with the one or more spectra to provide the, or each, processed spectra. The processing step comprises treatment of the raw spectra which improves the capability of the subsequent comparison stage. The processing step may comprise one or more of: normalisation and/or background subtraction. Preferably multiple output spectra are obtained and each spectrum is preferably wavenumber corrected.

The, or each, processed spectra is preferably further processed to provide one or more dimensionally reduced spectrum. The or each dimensionally reduced spectra is/are then compared to the known output spectrum/spectra in the control dataset.

The known output spectrum/spectra from a second blood or blood derivative sample preferably comprises a library of control spectra comprising both samples indicative of colorectal cancer and indicative of no colorectal cancer.

The method beneficially further comprises the step of outputting an indication of the determination or not of colorectal cancer in the subject. The output may for example be that there are colorectal cancer markers in the subject, there is no indication of the presence of colorectal cancer markers, and optionally diagnosis is not conclusive and further investigation is required. This enables a simple and easy to use triage tool to assist in deciding clinical needs and referrals. It can also incorporate previous spectral inputs from the subject to show progression/regression and/or treatment efficacy in relation to colorectal cancer.

Thus, the present invention enables identification of key Raman spectral signatures in the defined spectral range associated with diagnosing stages of colorectal cancer via the sampling of a patient's blood with clear adapted methodologies of both spectral acquisition and analysis.

According to a second aspect of the present invention there is an apparatus for determining an indication of the presence of colorectal cancer in a subject, the apparatus comprising a spectrometer for producing an output spectrum on a blood or blood derivative sample obtained from the subject and a processor configured to compare the output spectrum to a control dataset comprising a plurality of known output spectra derived from blood or blood derivative samples of a first plurality of subjects having colorectal cancer and a second plurality of subjects not having colorectal cancer, the apparatus arranged to output an indication of whether the subject has colorectal cancer.

The apparatus preferably further comprises a data storage device for storing the output spectrum and control dataset.

The spectrometer is preferably a Raman spectrometer.

The output spectrum is preferably taken at one or more wavenumbers or one or more ranges of wave numbers.

There preferably further comprises a receptacle for holding the blood or blood derivative sample, where the receptacle comprises a well. The well may be defined by a metal, wherein the metal is preferably stainless steel. The well depth may be between 4 mm and 8 mm, even more preferably between 5 mm and 7 mm, and even more preferably substantially 6 mm. The well diameter is preferably between 5 mm and 9 mm, even more preferably between 6 mm and 8 mm, and even more preferably substantially 7 mm.

The well is preferably defined in a sample holder, where there are a plurality of wells define in the sample holder. A cooling arrangement is preferably provided for cooling the sample holder. Advantageously, it has been found that cooling produces stable spectra readings, less variability and hence a better discrimination in the model. The cooling arrangement preferably comprises a cooling plate.

The spectrometer preferably comprises at least one laser light source and ideally a plurality of laser light sources. The laser light source(s) may be arranged to emit light in the visible wavelength band and/or the infrared wavelength band, thus, typically different laser light sources emit at different wavelengths. Accordingly, the light sources may comprise a first and second light emitter. The laser light source may comprise a 785 nm and/or 532 nm laser light source(s).

In yet a further preferred embodiment, the light source of the spectrometer is preferably focussed at between 1.1 and 1.3 mm above the bottom of the well, and even more preferably at approximately 1.2 mm above the bottom of the well. The bottom of the well is the lowermost point at which blood or blood derivative can locate in the well.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith. Moreover, unless stated otherwise, any feature disclosed herein may be replaced by an alternative feature serving the same or a similar purpose.

Aspects of the present invention will now be described by way of example only with reference to the accompanying drawings where:

BRIEF SUMMARY OF THE DRAWINGS

FIG. 1 is a presentation of a series of spectral acquisitions taken from an identical liquid sample. The upper set of acquisitions identified with reference numeral 2 indicate the varying response associated with raw data (left-intensity axis), and the lower set of acquisitions represented by reference numeral 4 indicate the spectra following pre-processing and normalisation (right-intensity axis).

FIG. 2 is a graphical representation of a partial spectral output from a normal control of a subject not suffering from colorectal cancer and a subject suffering from colorectal cancer. This shows the complexity of peak shape, peak intensity and peak position and thus the requirement for the application of building a model to incorporate the discrimination of the spectra and associated cohorts using appropriate application of Partial least squares Discriminant Analysis (PLS-DA). In particular this Figure shows the two solid lines representing the spectrum associated with the control dataset compared to the spectrum associated with a cancer sufferer. It is apparent that at the majority of wavenumbers the lines overlap with little variation in intensity. However, at certain wavenumber ranges such as between 1500 $cm^{-1}$ to 1720 $cm^{-1}$ there are differences in spectral output indicative of colorectal cancer. It is noted however that analysis of the wavenumbers in the range of 610 $cm^{-1}$ to 1720 $cm^{-1}$ is beneficial as wavenumbers where intensity matches can also be used in the determination of the indication of colorectal cancer.

FIG. 3 is a schematic flow diagram of the steps to determine whether a patient has colorectal cancer or shows progression or regression of colorectal cancer. Alongside the flow diagram are graphical representations of each of the steps.

Step 1 represents obtaining Raman spectra from a patient sample. As an example five repeat spectra are taken for each sample. This is plotted under Step 1 showing a series of spectral acquisitions. In Step 2 a processing step is carried out upon the multiple spectra as described in more detail later in the specification under the heading 'Data Pre-Processing' which makes the spectra comparable meaning that five spectra for each patient are maintained but the effects, for example, of sampling influences such as fluctuating laser power are accommodated.

All spectra are subsequently fed into the diagnostic model as presented in Step 3 where each spectrum has a dimensional reduction. In the exemplary diagnostic model, each spectrum becomes a dot. In this step a "training set" are the spectra that make up the model and the "test set" are the unknown samples and a comparison is carried out between the "test set" and the "training set" where the model determines which diagnostic group the unknown sample are most like. The contoured lines in the graphical representations represent the respective diagnostic groups.

In Step 4 the model presents an output wherein the diagnostic decision is output in a form indicating the likelihood or not of the sample indicting colorectal cancer. For example, a result of '1' is indicative of cancer and the output of '2' would be indicative of no cancer.

From the values of sensitivity and specificity are presented in order to identify how accurately the model completes this analysis.

Figure 1:
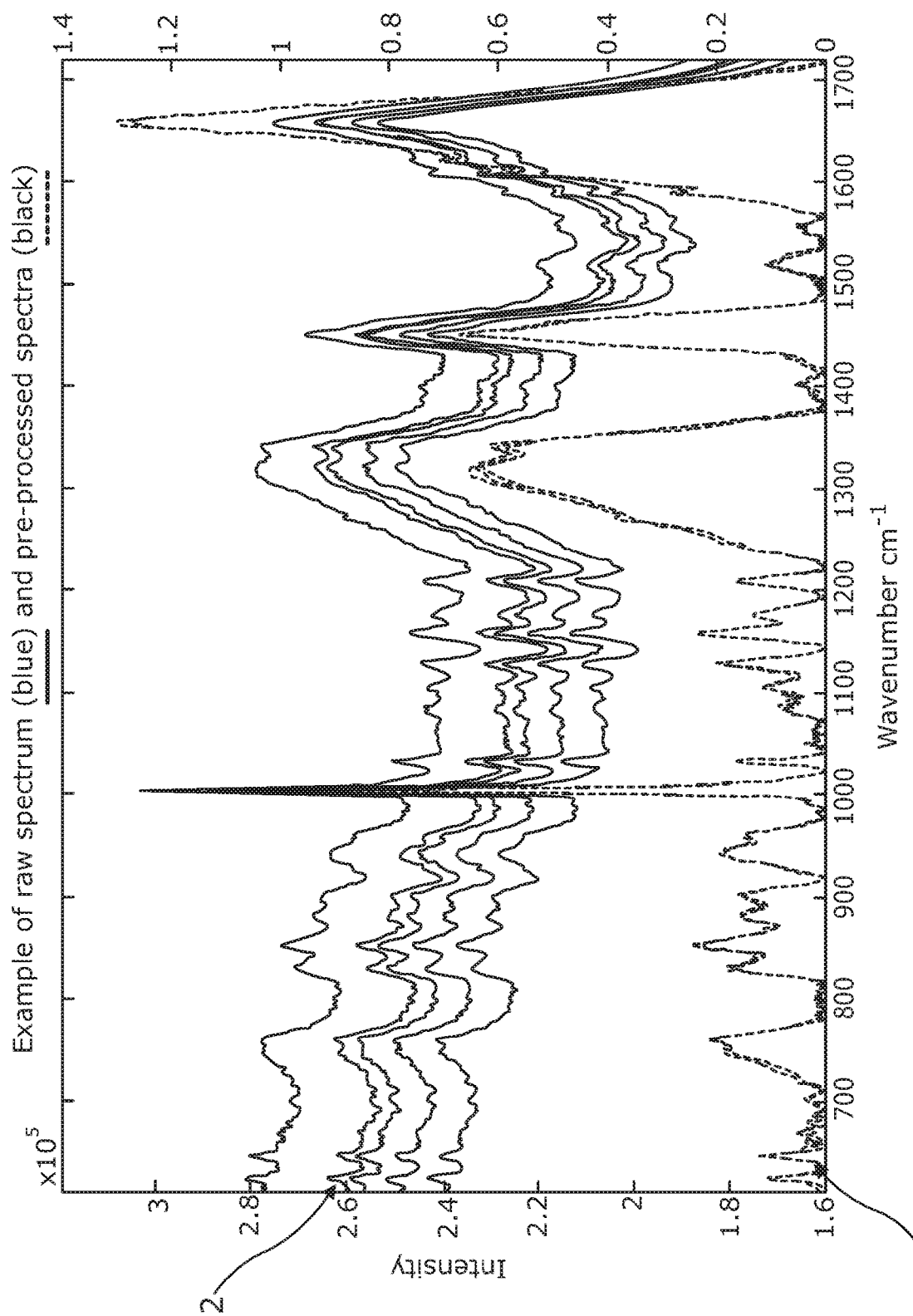
FIG. 1 is a graphical illustrative representation of a typical output spectrum from analysis of the blood derivative serum showing both the raw data and the pre-processed data (in this case rolling circle filtered and normalised as will be described subsequently). The data reproducibility is dependent on the sampling methodology and sample holder constructions that have been presented.
Figure 2:
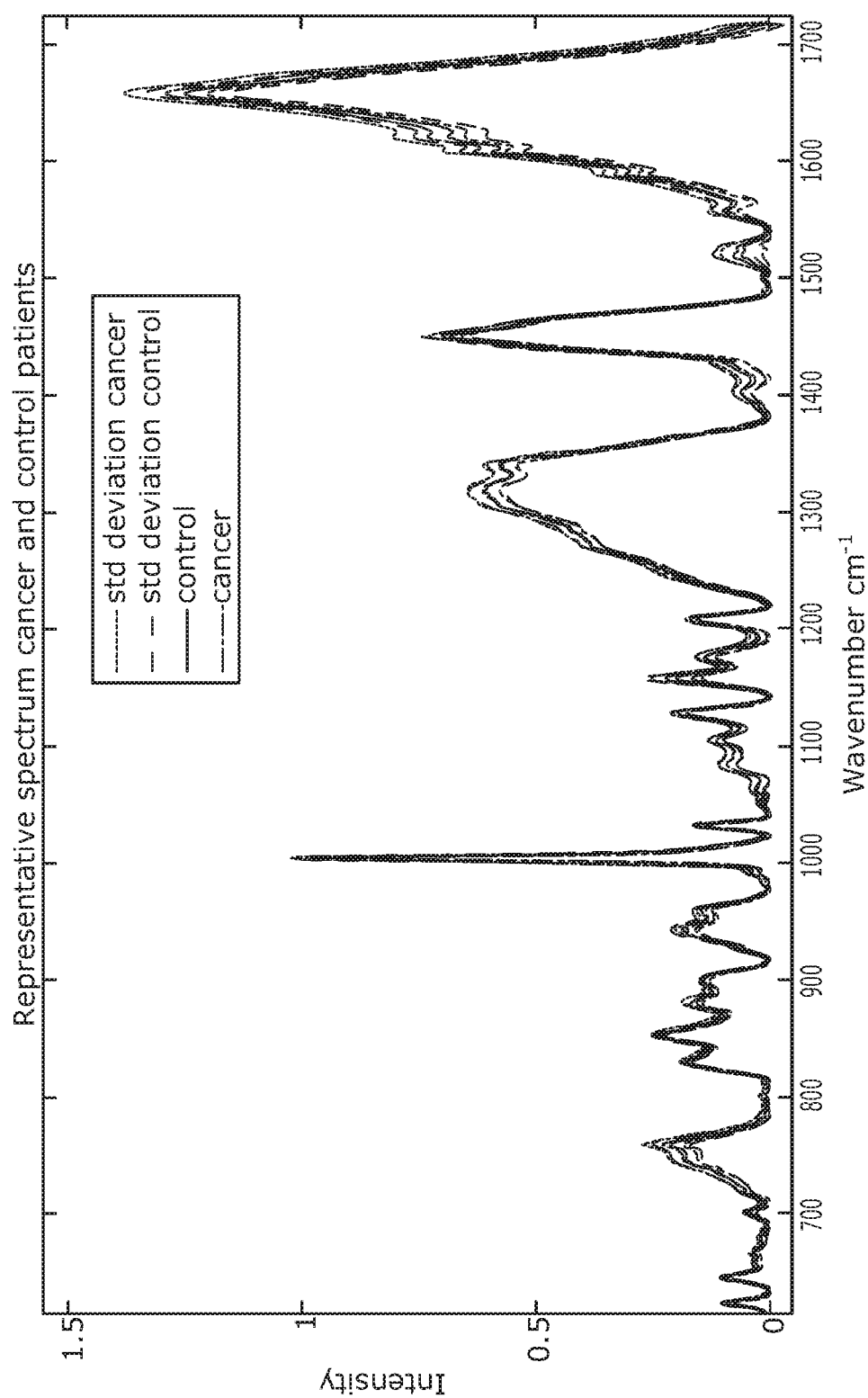
FIG. 2 is a graphical representation of a comparison between a normal control of a subject not suffering from colorectal cancer and a subject suffering from colorectal cancer, and also shows the standard deviations for both.
Figure 3A:
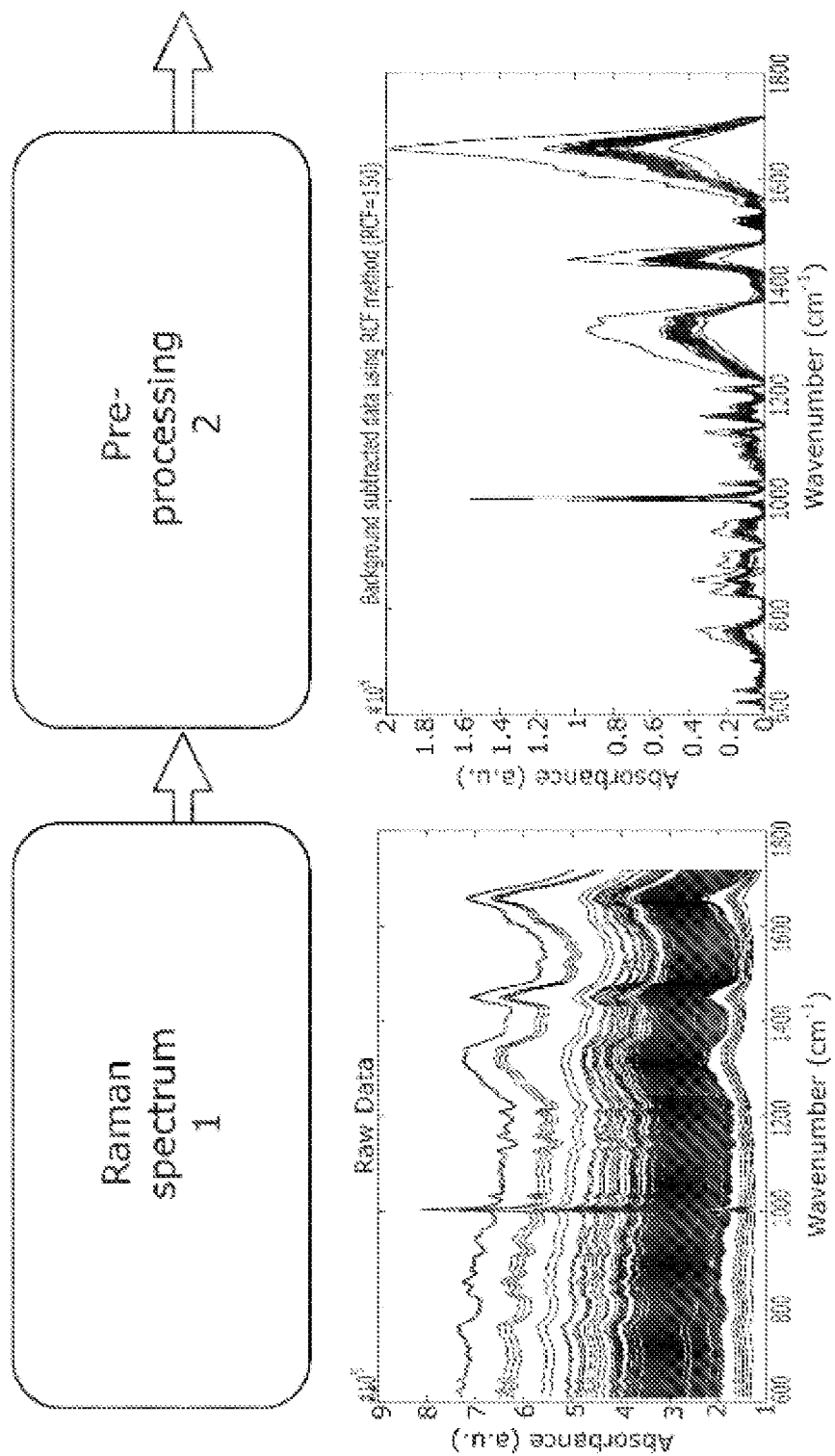
FIGS. 3A-3C are schematic flow charts and graphical representations of the processing steps carried out upon obtaining spectra from a patient.
Figure 3B:
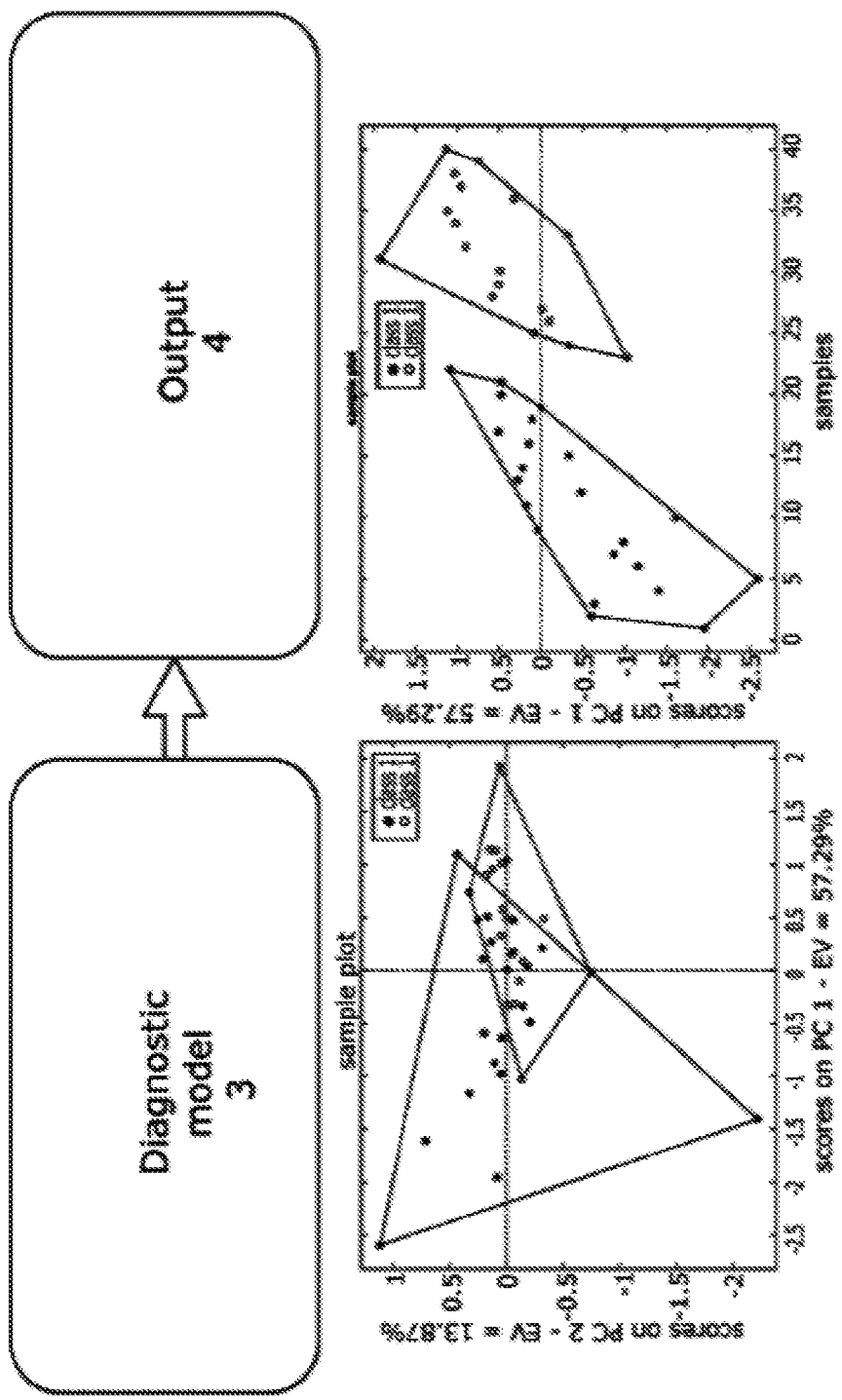
Figure 3C:
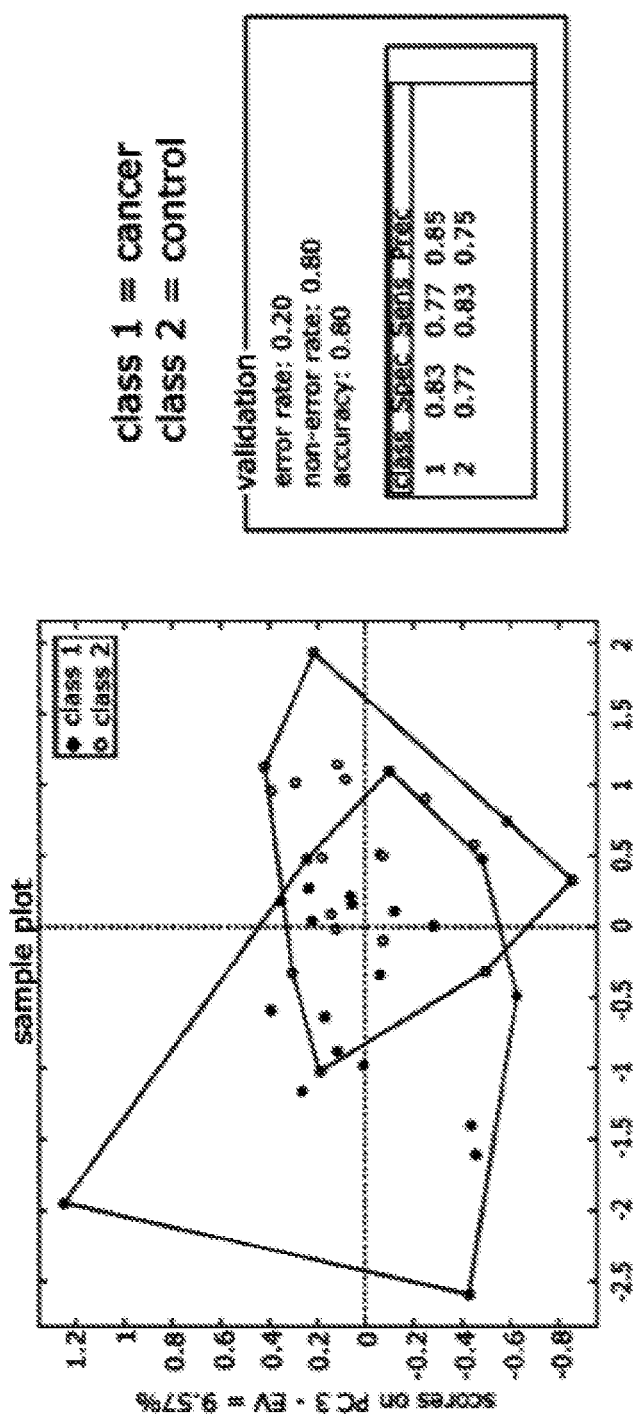
Figure 4:
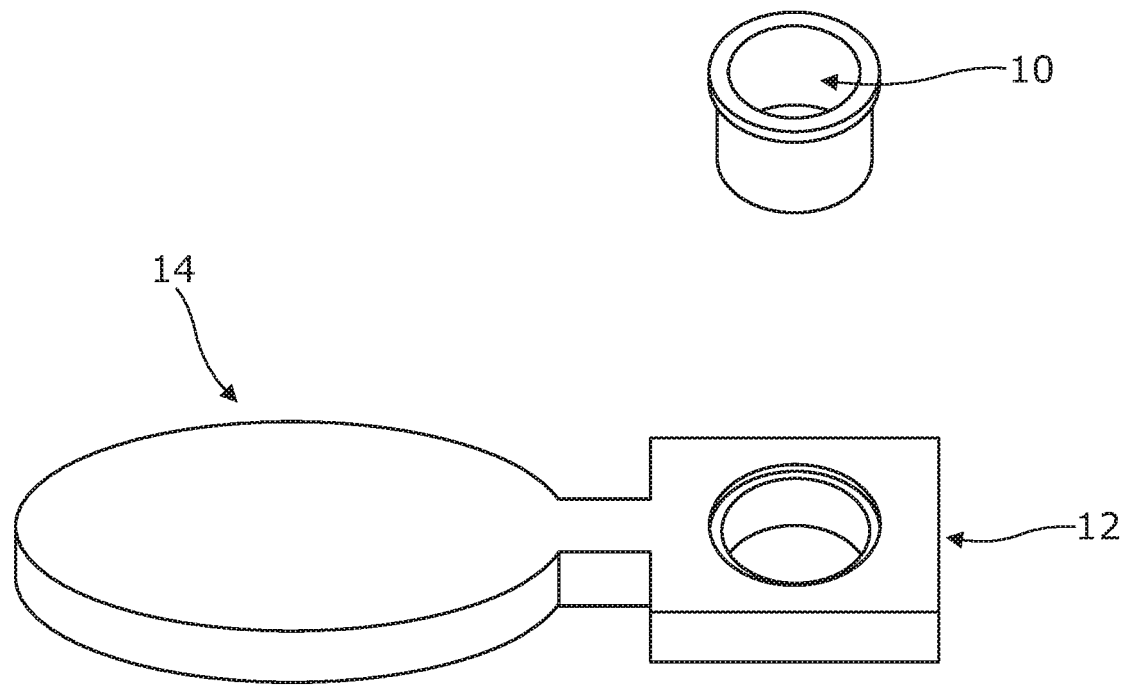
FIG. 4 is a schematic perspective representation of a single well for use with an exemplary embodiment of the present invention.

Referring to FIG. 4 there is an illustrative representation of a well 10 of substantially circular form comprising a metal such as aluminium or stainless steel. The well 10 may be received into a support structure 12 together forming a sample holder 14. The support structure 12 may comprise a material different to that of the well 10, and may, for example, be plastic. The well diameter is preferably approximately 7 mm and has a depth of substantially 6 mm.

Figure 5:
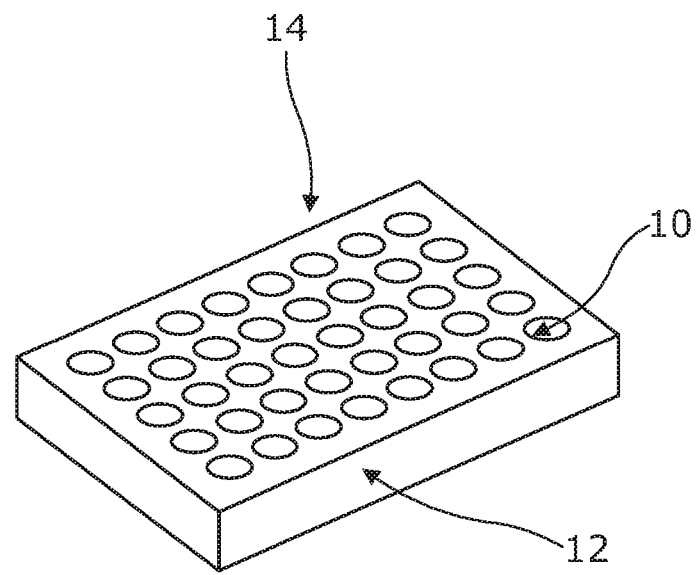
FIG. 5 is a schematic representation of a sample holder including a plurality of wells for use in an exemplary embodiment of the present invention.

Referring to FIG. 5, a sample holder 14 is shown having an array of wells 10 therein. The wells 10 may be integrally formed with the support structure 12 or may alternatively be mounted within the support structure 12.

Figure 6:
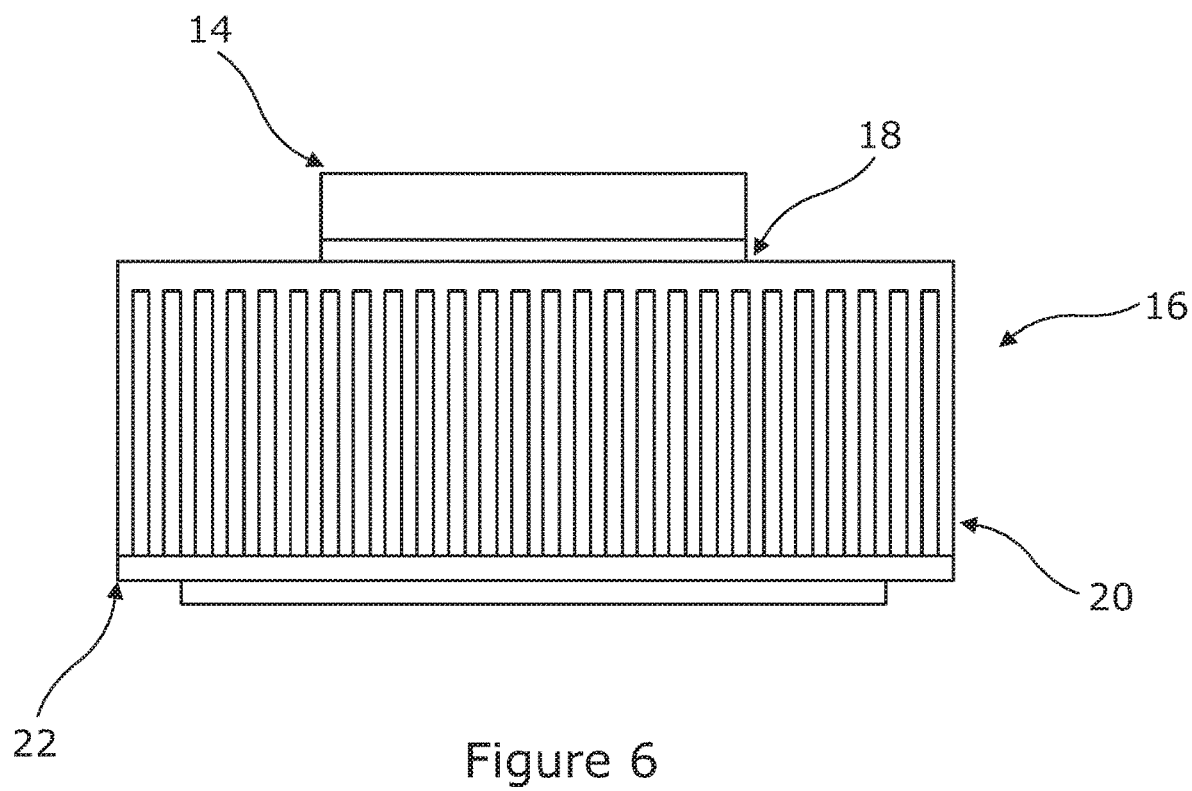
FIG. 6 is a schematic side view of a sample holder and cooling arrangement for use in conjunction with an exemplary embodiment of the present invention.

Referring to FIG. 6, the sample holder 14 is beneficially provided adjacent to a cooling structure 16 which may comprise a Peltier plate 18 adjacent to the sample holder 14 and in communication with a heat sink 20. The heat sink 20 is then supported by a base plate 22.

Figure 7:
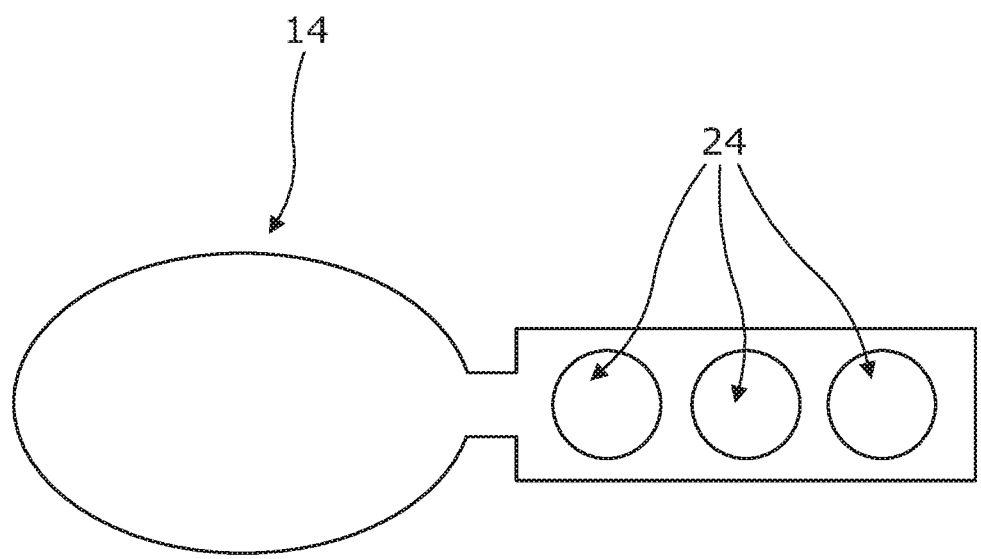
FIG. 7 is a schematic plan view of a sample holder according to an alternative illustrative exemplary embodiment of the present invention.
Figure 7:
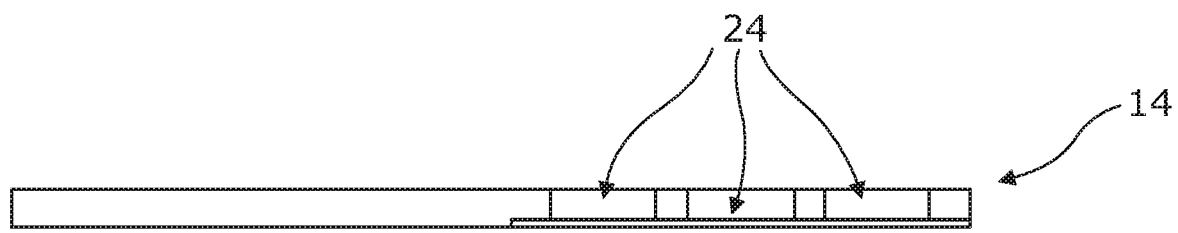

Referring now to FIG. 7, there is a plan and side view respectively of an exemplary embodiment of a sample holder 14 particularly for use with analysis of a dry blood or blood derivative sample. The sample holder 14 is preferably metallic and in the exemplary embodiment comprises three regions 24 where the blood or blood derivative sample is deposited and dried and subsequently analysed.

Figure 8:
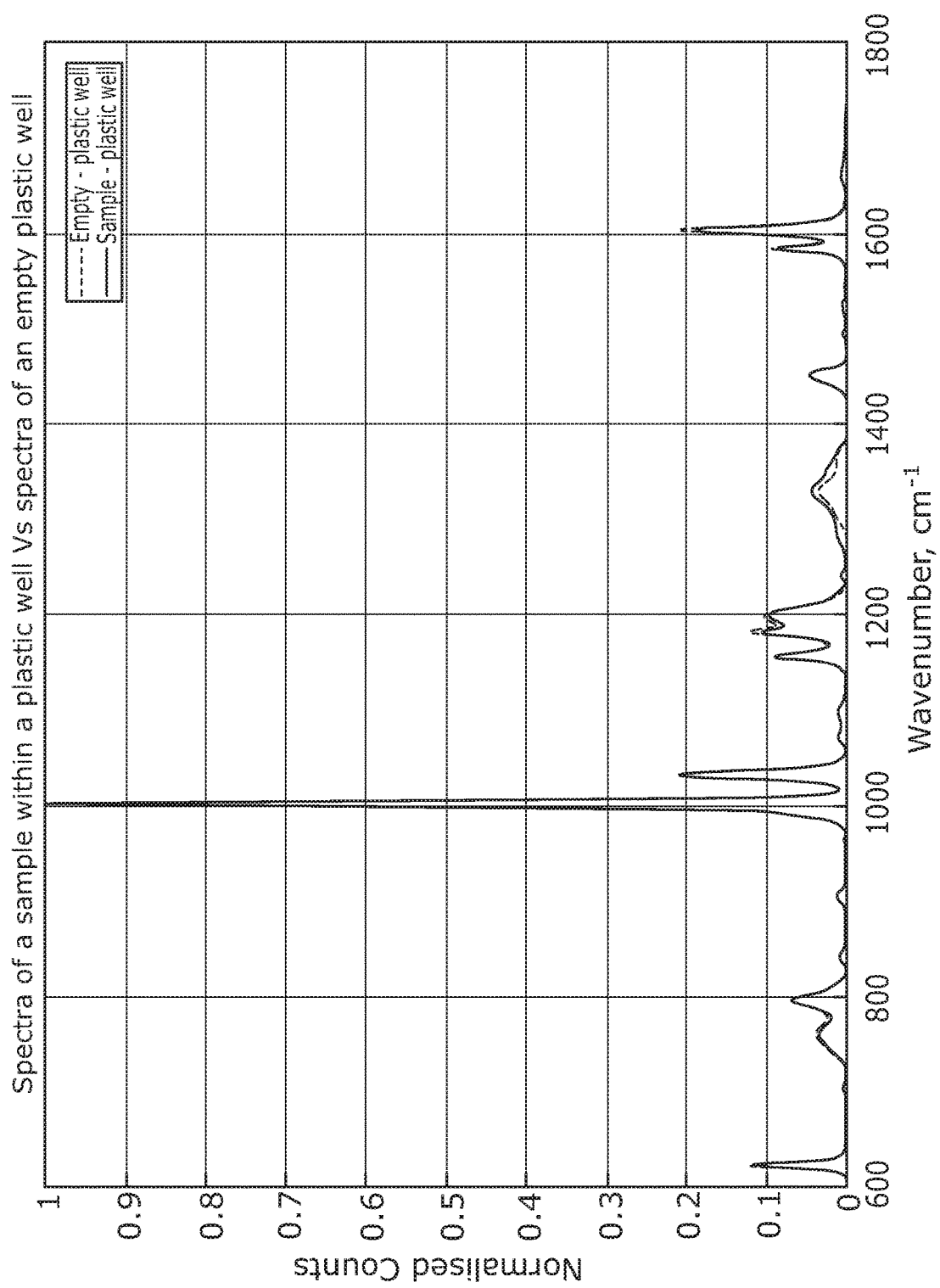
FIG. 8 shows Raman spectra when using plastic material well plates to exemplify the effect of well material on spectra readings.

Referring to FIG. 8, the materials used in well manufacture have been shown to drastically effect spectra readings. In contrast to metal wells, as shown in the spectra of the other figures, when using plastic material wells for readings no serum sample spectra is observed, with the signal dominated by inherent anomalies arising from the plastic of the well (as observed in absence of sample). This demonstrates that the use of metal wells is essential for Raman analysis.

Figure 9:
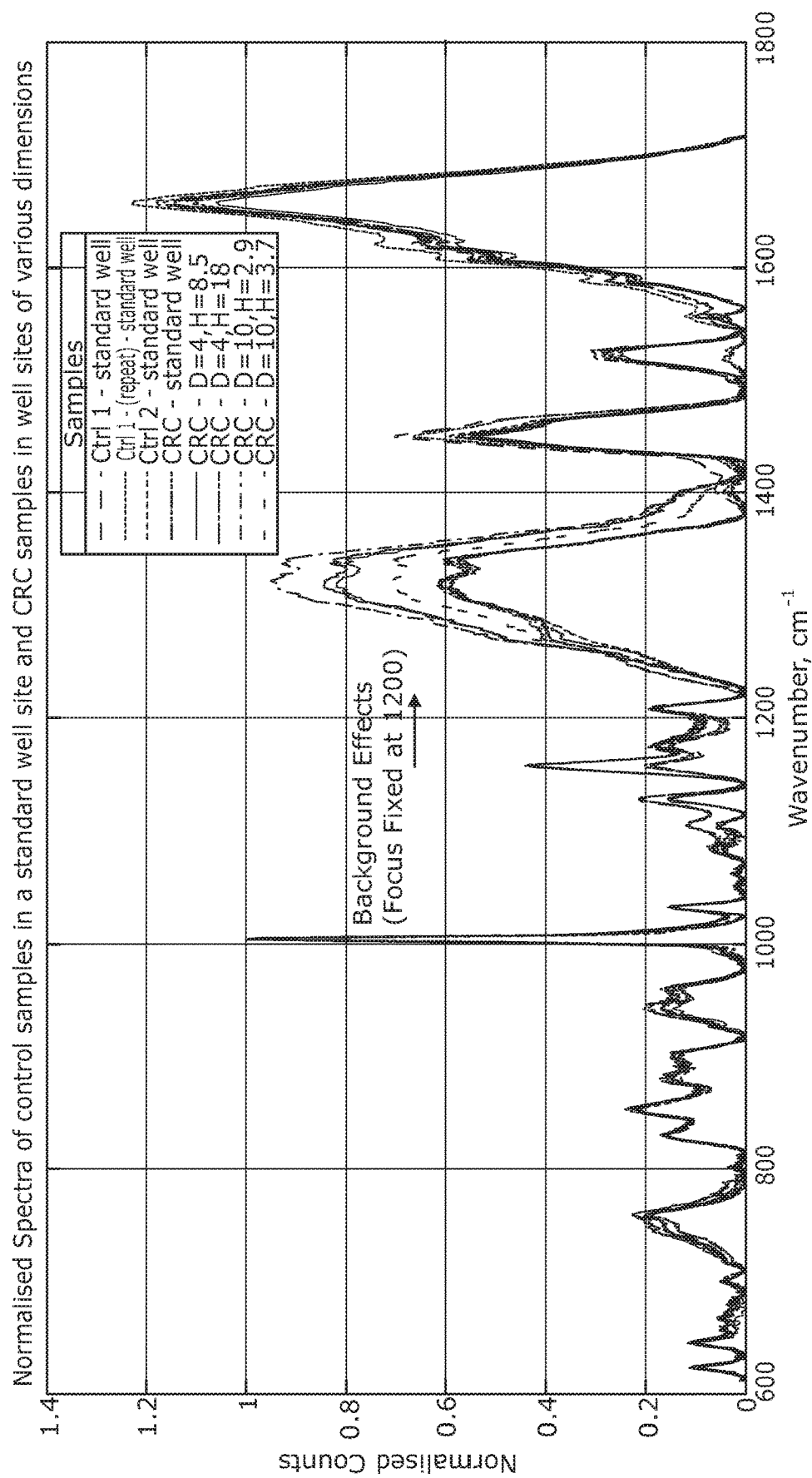
FIG. 9 shows the effect of well design on the spectral response of the serum sample. i.e. the dimensions of the well should be tailored to achieve a spectral response.
Figure 10:
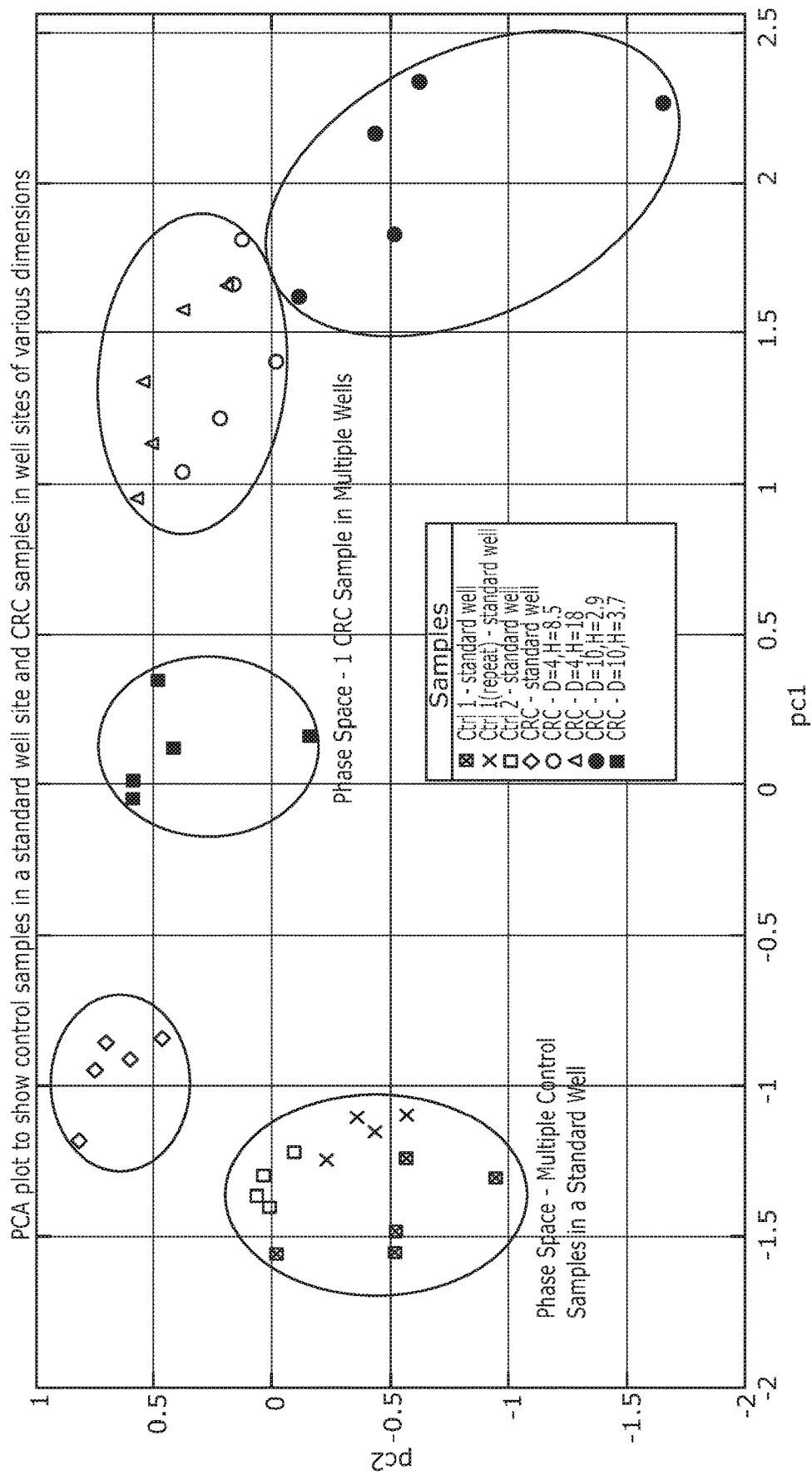
FIG. 10 shows the principle component analysis (PCA) graph of the influence of well dimensions and indicates the 5 spectra taken for each well design and sample.

Referring to FIG. 9, it is shown that careful consideration must be given to the effect of well design on the spectrum response of the sample i.e. the design of the well must be tailored to achieve a spectral recording, which maximises serum spectral recording over background. The spectra (background subtracted and normalised) demonstrate the variation of the background signature when different wells are used. The results are for samples of non-cancer controls (2 controls: Ctrl 1 &2) vs a colorectal cancer (CRC) sample when contained in different sized wells. D denotes well diameter and H denotes well height (i.e. depth). Well dimensions were compared to a standard well, having a depth of 6 mm and diameter of 7 mm. The variations seen in the spectra for identical serum samples are the result of the different well dimensions. Spectral recordings between 1200 and 1400 cm-1 show most variation including masking of spectral signatures of the serum when the dimensions of the well exceed the claimed amount. Spectra were also repeated in each well to consider reproducibility issues. This is confirmed by the PCA analysis as shown in FIG. 10 (please note the greyed areas show the generation of the CRC serum when measured in different containers and hence a large dispersion across the Principal Component Analysis (PCA) graph. The circles demonstrate the range of variation of the repeat measurements in wells and indicate the greatest range was with well dimensions that are outside of outside of well diameters in the range 5 mm to 9 mm and well depths in the range 4 mm to 8 mm. i.e. wells smaller or bigger on these dimension produce the largest spectral variations. The purpose of the Raman analysis is to discriminate accurately between cancer samples and non-cancer, and inappropriate well design makes a viable diagnostic difficult to achieve because of unreproducible spectra results. The standard well responses of CRC and Ctrl (1&2) give discrimination on the PC2 axis, which was not observed when using other well dimensions outside the critically defined parameters.

Figure 11:
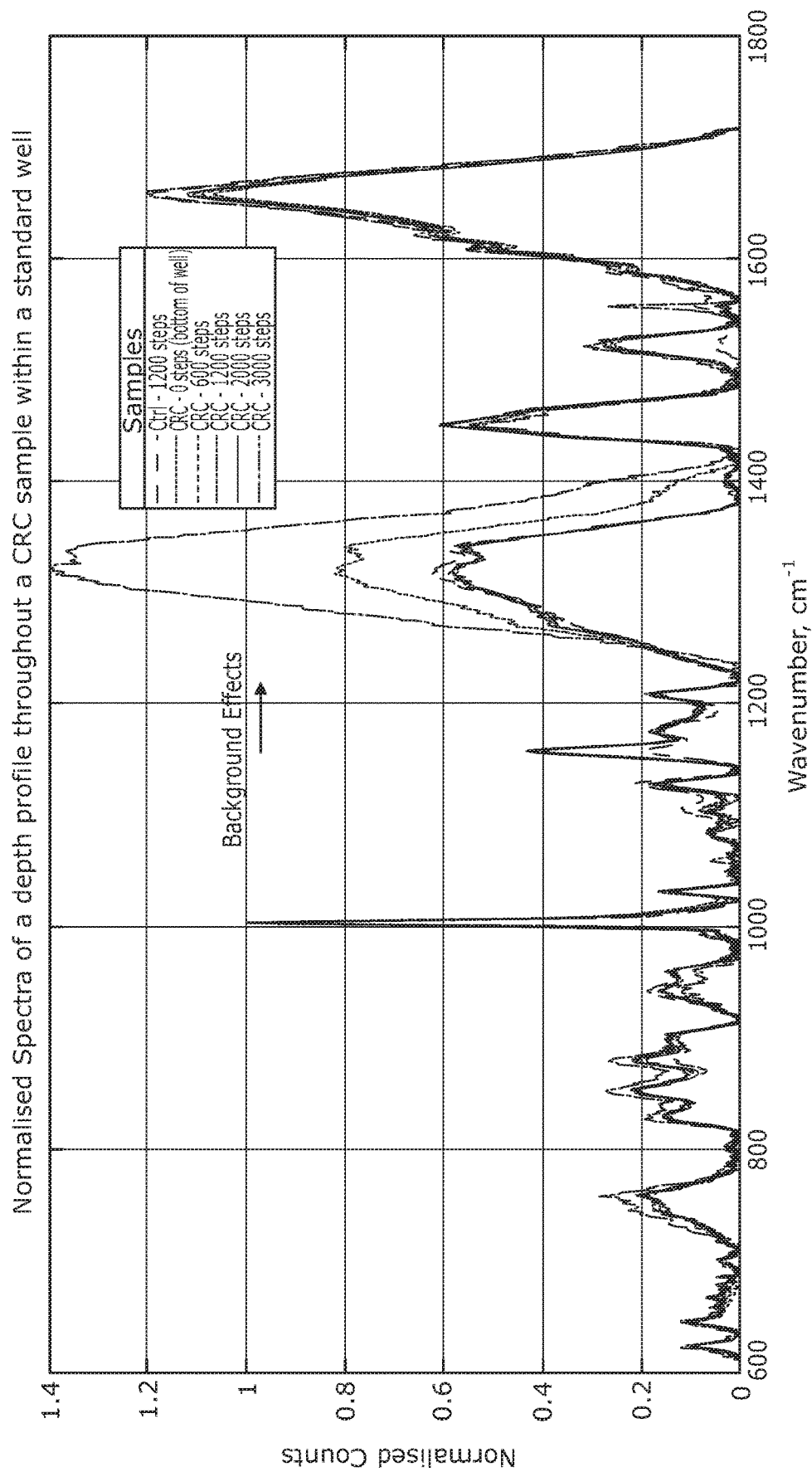
FIG. 11 shows comparison of spectra readings using different focal depths.
Figure 12:
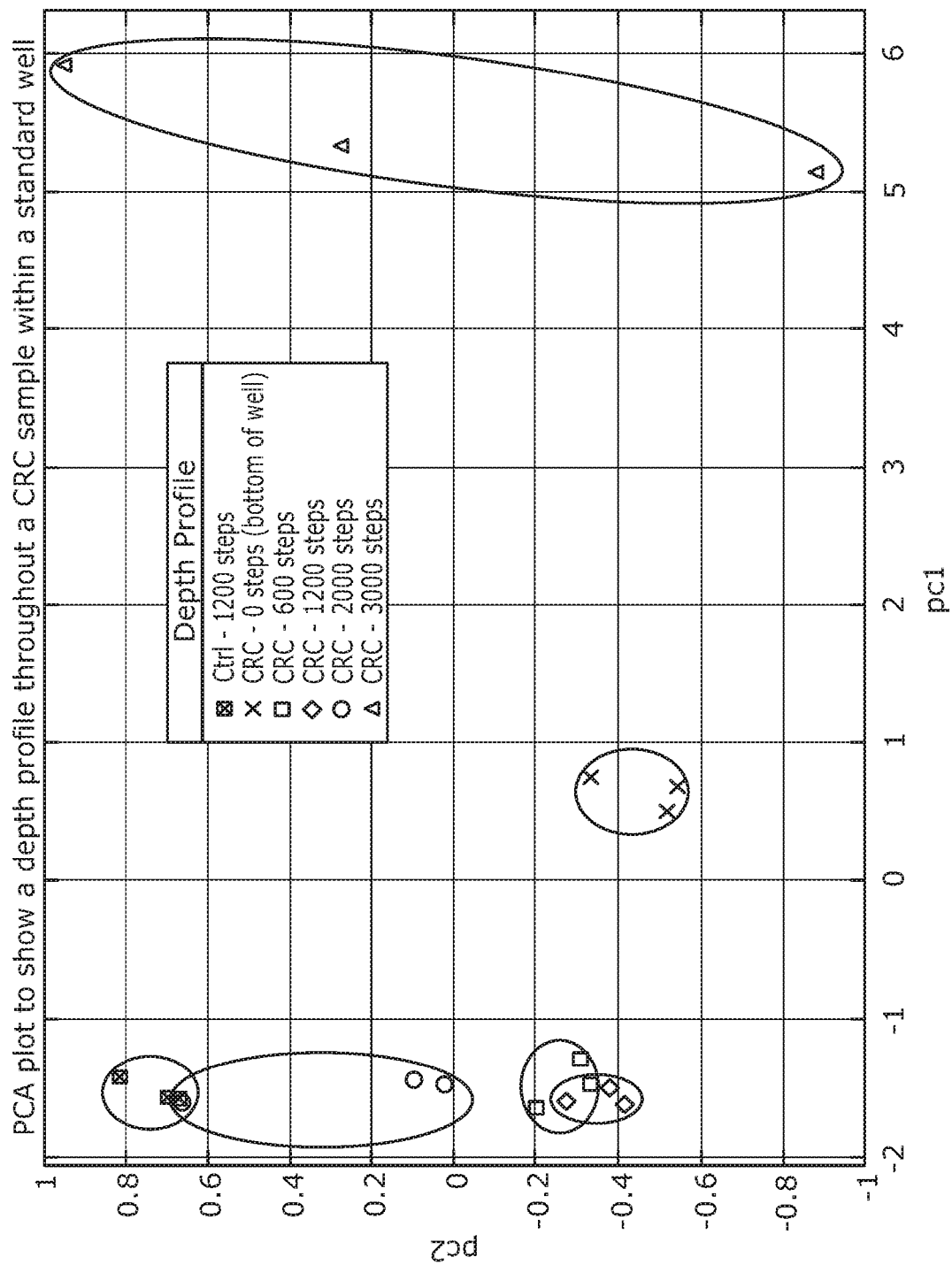
FIG. 12 shows the principle component analysis (PCA) graph of the influence of focal depth on spectra.

Referring to FIGS. 11 and 12, if the standard well size is used with a non-optimised focus then the background signatures becomes an issue. Of particular note, when focussed on the surface of the liquid and also at the base (lowest depth) of the well, the signatures are most affected. Focus steps away from the base (600, 1200) translate to an optimum focus of 1.1 to 1.3 cm. The PCA plot for well focus depth (FIG. 11) demonstrates the variability of repeated measurements under identical conditions. The overlap of the 600/1200 circles for a CRC sample indicates that focus is optimised in this region and variability is reduced, the optimum conditions for a control sample, show discrimination from the CRC and also a low variability. The increased scatter in the PCA for 2000 and 3000 steps show they are not viable focus settings. The bottom of the well, whilst not showing large variability is subject to background components, as shown on the previous spectral plot.

Figure 13:
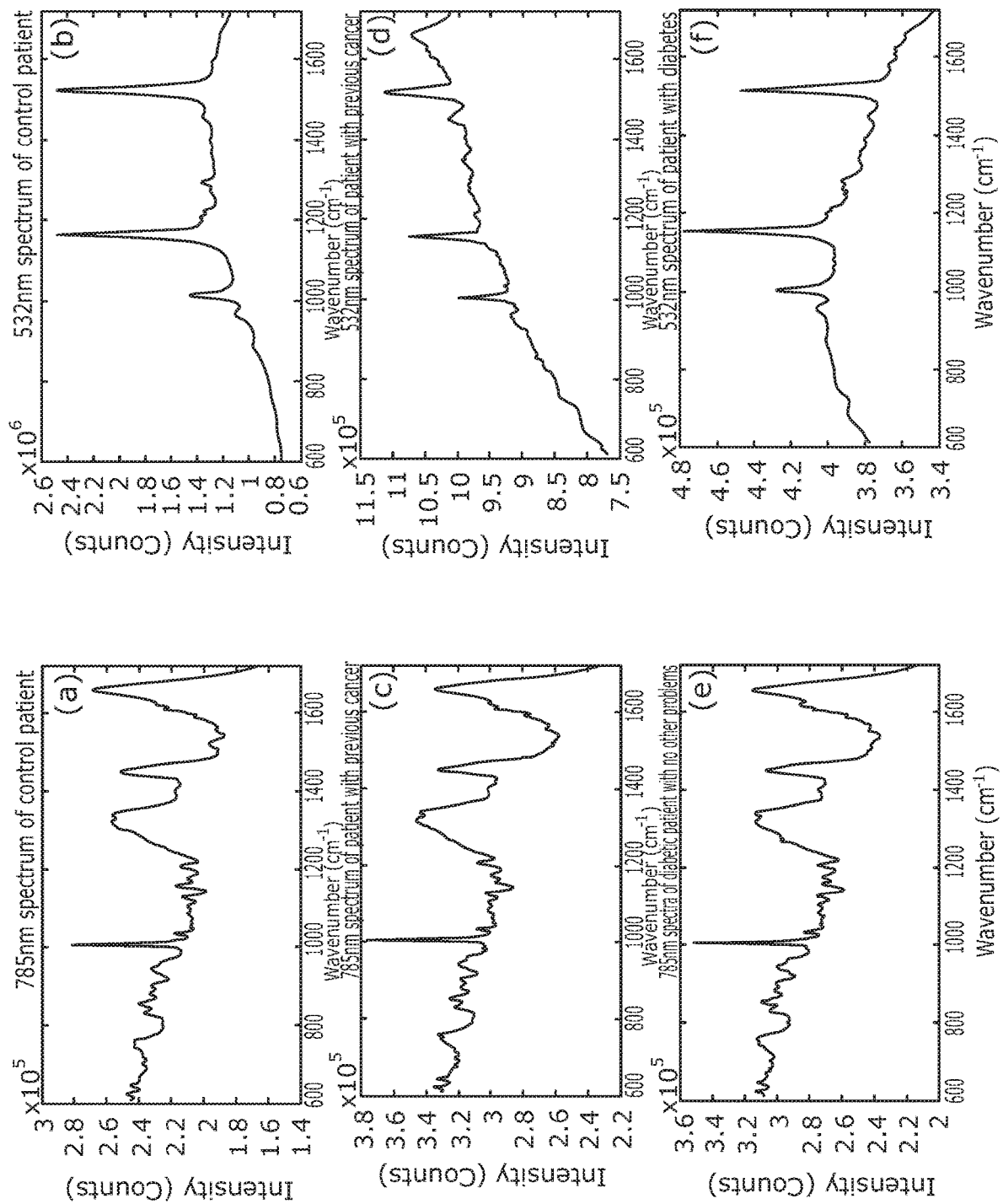
FIG. 13 shows that utilising double spectra readings at 532 nm and 785 nm to improve discrimination in patient samples who exhibited additional insult, such as prior cancer diagnosis or other illness.

Referring to FIG. 13, the raw spectra shows that the two-wavelength approach (visible and infra-red) produces different fingerprint responses. By inspection of the raw data, the 785 nm samples look very similar, but the 532 nm spectra have very different background signatures, where the effects of illness are clear and thus are incorporated into the model to improve discrimination. Spectra of a control patient with no other health issues with the (a) 785 nm and (b) 532 nm laser; Spectra of a control patient who had previous cancer and had chemoradiotherapy (CRT) with (c) 785 nm and (d) 532 nm laser; and spectra of a control patient with diabetes with (e) 785 nm and (f) 532 nm lasers.

Figure 14:
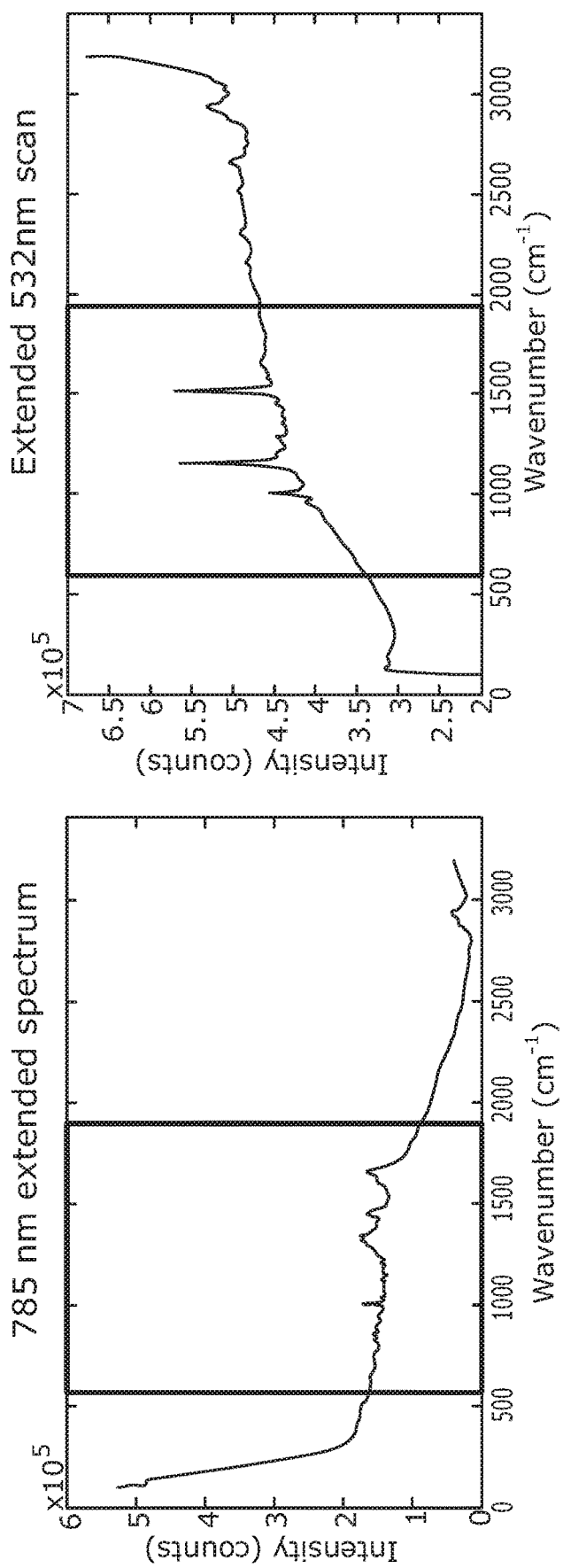
FIG. 14 shows the effect of the spectral wavenumber range that provides optimum readings.

Referring to FIG. 14, the output spectrum is preferably recorded between 610 $cm^{-1}$ and 1718 $cm^{-1}$. This range has been shown to encompass the fullest spectral output that allows reproducible discrimination.

Figure 15:
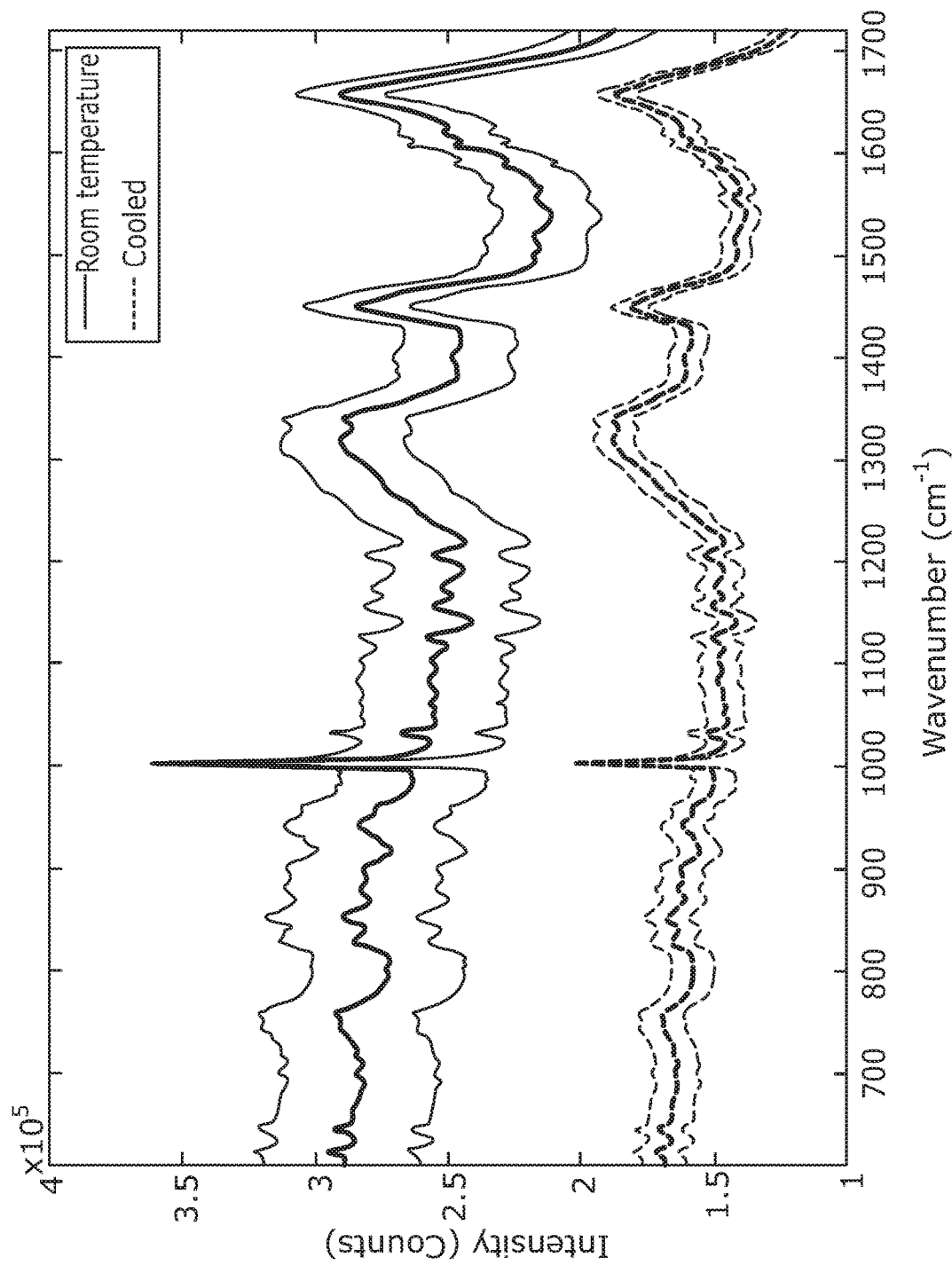
FIG. 15 shows the effect of temperature on reproducibility of spectra.

Referring to FIG. 15, it is shown that the spectral variability (colour envelope) as a function of temperature. Room temperature (unstabilised) creates a large variation in the spectra, which ultimately affects the model. Cooling produces stable data, less variability and hence a better discrimination in the model.

Figure 16:
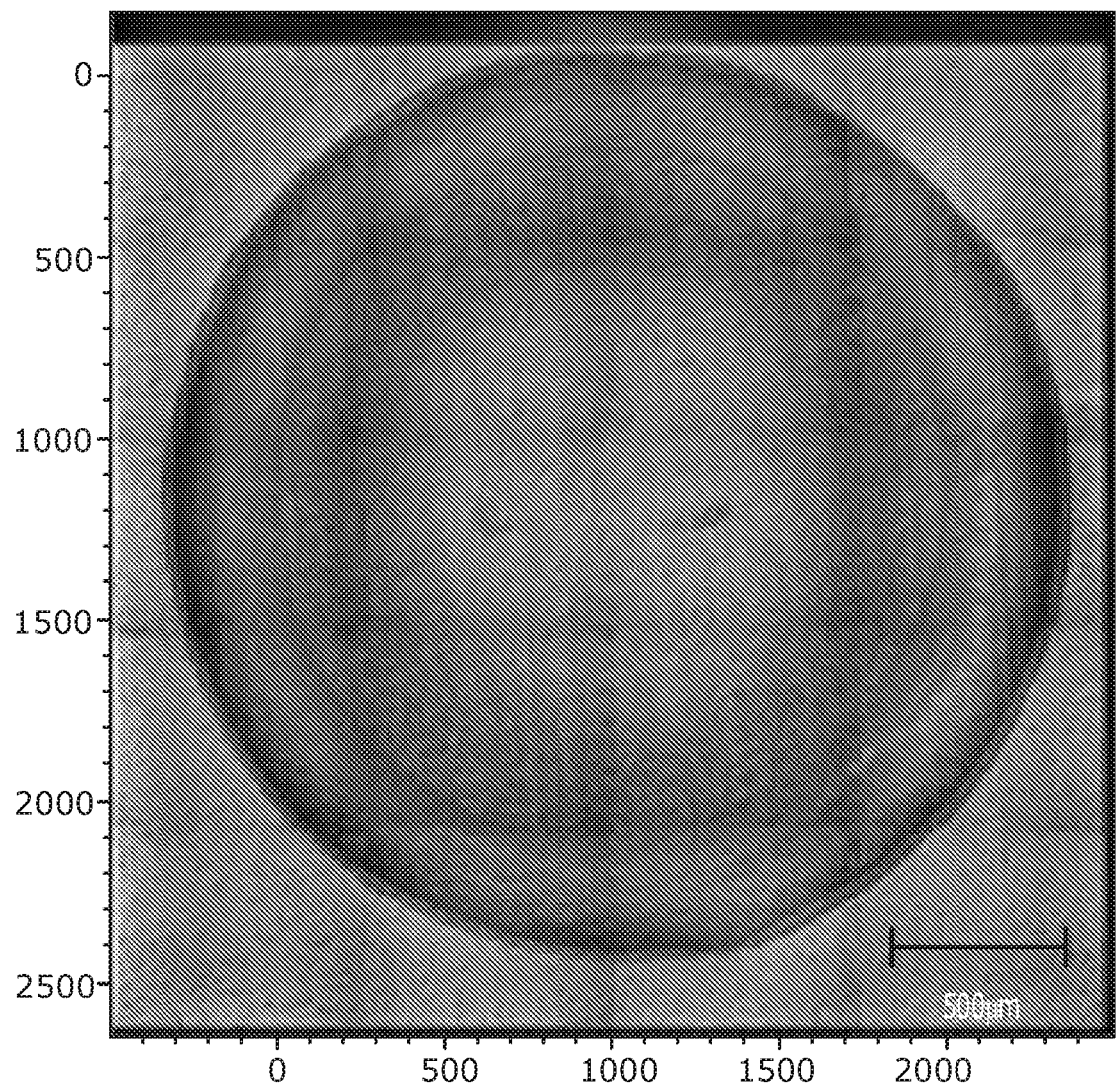
FIG. 16 shows spatial variance when taking spectra from dry spot samples.

Referring to FIG. 16, variance in spectra can occur when analysing different areas of dryspot samples not apparent in liquid samples. PC loading built into imaging—displays spatial variance—dark region is region of lower variance and is thus best to analyse for reproducibility. The image demonstrates the dark ring, i.e. the area of least variance and thus best location to derive spectra for analysis when sampling from a dry spot of serum in order to achieve reproducibility.

The following description describes illustrative steps for obtaining data from serum (or blood or other blood derivative) samples, and subsequently analysing the results for production of a model which can be used for the claimed method of determining the presence or progression/regression of colorectal cancer. The diagnostic output will be measured in terms of sensitivity and specificity. The sensitivity is a percentage of true positive results that were correctly identified by the test. In this case the number of cancer patients identified as having cancer. The specificity is the percentage of true negative cases that were correctly identified by the diagnostic test. In this case the number of control patients that were correctly identified as control patients.

Sensitivity definition: Number of true positives divided by the sum of the number of number of true positives and the number of false negatives.

Specificity definition: Number of true negatives divided by the sum of the number of true negatives and the number of false positives.

(A) Sampling (Data Acquisition)

Serum Collection

Patient characteristics at time of sampling may define the accuracy of the resultant spectrum. Patients are preferentially fasted for 4 hours pre-sampling, be a non-smoker and not having diseases of the liver. Details of patient medication are also recorded. Blood samples are taken by a skilled phlebotomist via normal standard operating procedures. Vacutainer™ Serum Separator blood collection tubes were used to collect the blood. The collection tubes were then handled according to the manufacturer's best practice protocols in order to produce liquid serum. The serum samples were then left 30 minutes to coagulate.

Three different spectral analysis methods will now be described.

Raman Spectroscopy of Dry Samples (785 nm Laser)

A Renishaw In Via Raman Spectrometer equipped with a 785 nm and a 532 nm laser light source was used. Samples were spotted onto an aluminium foil based sample holder and left to dry at room temperature prior to spectral acquisition. Data points were collected using a 50× objective (Leica) that focuses a 785 nm (diode) laser beam onto the sample. The sample spot was then interrogated with 165-175 mW (100%) power with an exposure time of is in the spectral region between 610 $cm^{-1}$ and 1718 $cm^{-1}$. This was then averaged over 30 acquisitions to produce one spectrum. This process was then repeated across the sample droplet and can be extended to other deposited droplets on the sample stage. 10 replicates per sample are preferred. Preferably image recognition can also be employed to sample a specific area of the dried sample and increase reproducibility. The laser is used in spot mode and 10 random positions across the spots are selected. We pipette 3 spots and use 2-3 of them with up to 5 scans on each.

Raman Spectroscopy of Liquid Samples (785 nm Laser)

Liquid samples were pipetted into a receptacle in the form of a stainless-steel sample holder which had multiple wells. This was then placed into the spectrometer onto a stainless-steel cooling plate. Using a 10× dry objective (Leica) 785 nm laser light was focused to 1.2 mm above the base of the well into the liquid sample. Data points were then taken using 165-175 mW laser power for 5 s exposure time in the spectral region between 610 $cm^{-1}$ and 1718 $cm^{-1}$. This was then averaged over 30 acquisitions to produce one spectrum. This process was then repeated to produce 5 replicates per sample and is used in the diagnostic model to check on degree of spectral variances associated with 'sampling' reproducibility.

Raman Spectroscopy of Liquid Samples (532 nm Laser)

Liquid samples were pipetted into a receptacle in the form of a stainless-steel sample holder which had multiple wells. This was then placed into the spectrometer onto a stainless-steel cooling plate. Using a 10× dry objective (Leica) 532 nm laser light was focused to 1.2 mm above the base of the well into the liquid sample. Data points were then taken using 45-55 m W laser power for 0.6 s exposure time in the spectral region between 610 $cm^{-1}$ and 1718 $cm^{-1}$. This was then averaged over 120 scans to produce one spectrum. This process was then repeated to produce 5 replicates per sample and is used in the diagnostic model to check on degree of variances associated with 'sampling' reproducibility.

(B) Analysis

Descriptions of the analysis of Raman spectra can be split into 3 categories:
1. Data pre-processing
2. Diagnostic Model building
3. Model testing

1. Data Pre-Processing

Two alternative methods are presented as the preferred methodology for subtracting background fluorescence from the spectra acquired. These are determined to be better than alternative methods (such as simple background fitting with a polynomial function). Two further procedures are then described in order to allow the spectra to be compared by minimising the effects of 'sampling' influences (such as fluctuating laser power). This process is known as normalisation. The two methods of normalisation described are vector-normalisation and peak-maximum normalisation. As with background subtraction both methods are found to be better than alternative methods.

1.1 Data Pre-Processing—Derivative Spectra

Spectral data was acquired using the methods previously described. All spectra were wavenumber corrected using developed software. The raw data from the spectrometer has an x-axis that slightly differs each time a scan is run due to the CCD detector on the system. The wavenumber correction allows for this allowing a direct comparison between samples by creating a single x axis for sample comparison. The spectra were then background subtracted using a 2nd order polynomial and 9 point Savitzky-Golay derivative algorithm and were then vector normalised. Vector normalisation helps to allow comparison between samples by making the area under each spectrum equal to 1. This then allows the comparison of overall spectral shape between different samples to determine compositional changes without the effects of 'sampling' influences dominating spectral discrimination.

1.2 Data Pre-Processing—Rolling Circle Filter

Spectral data was acquired using the methods previously described. All spectra were wavenumber corrected. The spectra were then background subtracted using a high pass rolling circle filter with a specifically chosen radius, preferably of 150, in order to subtract background fluorescence from the spectral data. This type of background can change between sample spectra and can dominate the discrimination procedure and hence mask the sensitivity required for cancer discrimination. Additionally, these spectra were then normalized to the peak at about 1004 $cm^{-1}$ attributed to phenylalanine in some cases and vector normalized in other cases, depending on the diagnostic model performance. All normalization techniques help to standardise the spectra in order for them to be suitable for discrimination comparisons. In the case where we would like to look at the ratios to a particular peak (1004 $cm^{-1}$) this type of normalisation was used. This type of normalisation makes the peak at 1004 $cm^{-1}$ in each spectrum equal to 1. Therefore, the intensity variations between the peak at 1004 $cm^{-1}$ and all other peaks can be compared more easily against the similarly processed controls, i.e. peak changes (intensity, width and lineshape) can be attributed directly to compositional changes in the sample rather than external 'sampling' influences such as non-cancer related sample changes and laser spectroscopy conditions.

2. Diagnostic Model Building

Pre-processed data is fed into PLS-DA (partial least squares discriminant analysis) using mean-centred data with 9 latent variables in order to produce the diagnostic model. This model is then cross validated using venetian-blinds cross validation in order to produce a model training dataset. The latent variables are considered to be the isolated components of the spectrum that are indicative of cancer. These are created within the model. This model is then cross-validated using venetian-blinds cross validation in order to produce a model training dataset. The cross validation acts as an internal validation to the model so the model doesn't give an over-prediction of the sensitivity and specificity of the test. The dataset used to train the diagnostic model is split into even groups during the validation. The model is then re-made leaving some of the groups out. The 'left out' groups are then used as a 'testing' dataset in order to see how well the model predicts the results without the full dataset. The sensitivities and specificities reported are those of cross-validated models. This method is preferred over other options due to the sensitivity and specificity that it can achieve.

3. Model Testing for the Detection of Colorectal Cancer—Dry Serum Samples

Raman spectra were taken from 3 μl droplets that had been dried as described above. Spectra were collected for patients who are confirmed to have colorectal cancer (n=30) and age matched controls who have a clear colonoscopy and no other signs of cancer (n=30). Using derivative spectra that have been vector normalized the cross validated diagnostic model produced a performance of a sensitivity of detecting cancer of 98% and a specificity of 92%. Using a rolling circle filter based pre-processing method with vector normalisation a sensitivity and specificity of 92% and 91% was achieved. Using a rolling circle filter based pre-processing and a 1004 $cm^{-1}$ normalization a sensitivity and specificity of 95% and 92% respectively.

Raman Spectroscopy for the Detection of Colorectal Cancer—Liquid Serum Samples Raman spectra were collected from patients with cancer and control patients (n=60) using the 785 nm laser source.

Spectra were then pre-processed using the rolling circle filter and peak normalization. After building a PLS-DA diagnostic model a sensitivity and specificity of 85% and 81% were achieved. This dataset was repeated with the 532 nm laser and results of 74% and 78% sensitivity and specificity were achieved using the same analysis routine. Consideration has also been made as to the use of two lasers for analysis of each sample which enables a more robust diagnostic. The use of different wavelengths promotes different responses from the sample and can achieve distinguishing of responses that may be affected by, for example, the effect of medication that a subject is taking.

It can therefore be seen that the proposed invention offers a robust discrimination tool for determining the onset or progression/regression of colorectal cancer and the best route as to how this is achieved. The results of the test can be outputted to a user requiring no further interpretation and may give an indication of the presence of colorectal cancer markers in the patient, no positive indication of colorectal cancer markers in the patient, or indicate a non-conclusive result meaning further investigation is required (for example this may include checking if patient medication is influencing the test, or whether the patient had followed appropriate pre-test conditions).

It will be appreciated that the colorectal cancer discrimination software may be updated upon analysis of an increasing number of clinical samples thus resulting in the model becoming self-learning.

Aspects of the present invention have been described by way of example only and it will be appreciated to the skilled addressee that modifications and variations may be made without departing from the scope of protection afforded by the appended claims.

The invention claimed is:

1. An apparatus for determining an indication of the presence of colorectal cancer in a subject, the apparatus comprising: a Raman spectrometer comprising a metal well configured for holding an unmodified liquid blood, serum, or plasma sample, wherein the metal well is substantially circular and has a diameter between 6 mm and 8 mm and a depth between 5 mm and 7 mm, wherein the metal well minimizes masking of spectral readings, thereby improving sensitivity and discrimination between cancer and non-cancer spectra; and a processor configured to compare an output spectrum of said sample to a control dataset comprising a plurality of unknown output spectra derived from unmodified liquid blood, serum, or plasma samples of a first plurality of subjects having colorectal cancer and a second plurality of subjects not having colorectal cancer; wherein the apparatus is arranged to output an indication of whether the subject has colorectal cancer from the comparison of the spectra.

2. The apparatus according to claim 1 wherein the metal well is defined in a sample holder, and wherein there are a plurality of wells defined in the sample holder.

3. The apparatus according to claim 2, further comprising a cooling arrangement for cooling the sample holder.

4. The apparatus according to claim 3, wherein the cooling arrangement comprises a cooling plate.

5. The apparatus according to claim 1, wherein the Raman spectrometer comprises at least one laser light source.

6. The apparatus according to claim 5, wherein said at least one laser light source is arranged to emit a first and second wavelength of light, the first wavelength of light different to the second wavelength of light.

7. The apparatus according to claim 5, wherein the Raman spectrometer comprises a laser light source, the laser light source comprising a 785 nm and/or a 532 nm laser light source.

8. The apparatus according to claim 1, wherein the well depth is 6 mm.

9. The apparatus according to claim 1, wherein the well diameter is 7 mm.

10. A method of determining an indication of the presence of colorectal cancer in a subject, comprising:
placing an unmodified liquid blood, serum, or plasma sample obtained from the subject in a Raman spectrometer well, wherein said well is metal and substantially circular having a diameter between 6 mm and 8 mm and a depth between 5 mm and 7 mm;
performing laser Raman spectroscopy on the unmodified liquid blood, serum, or plasma sample obtained from the subject in order to obtain at least one output spectrum;
comparing the output spectrum to a control dataset comprising a plurality of known output spectra, where the plurality of known output spectra are derived from the unmodified liquid blood, serum, or plasma samples of a plurality of first subjects having colorectal cancer and a plurality of second subjects not having colorectal cancer; and
determining whether the subject has an indication of the presence of colorectal cancer from the comparing.

11. The method according to claim 10, wherein the sample comprises serum.

12. The method according to claim 10, wherein said sample is cooled before and/or during sampling whereby a fixed temperature is maintained.

13. The method according to claim 10, wherein a light source of the Raman spectrometer is focused at between 1.1 and 1.3 mm above a bottom of the well.

14. The method according to claim 10, wherein the output spectrum is recorded between 610 $cm^{-1}$ and 1718 $cm^{-1}$.

15. The method according to claim 10, wherein the laser Raman spectroscopy subjects the sample to a first and second different wavelength of laser light to obtain a first and second spectrum, where the comparison step uses the first and second spectrum in the comparison.

16. The method according to claim 15, wherein the first wavelength is in the wavelength band of visible light, and the second wavelength is in the wavelength band of infrared light.

17. The method according to claim 15, wherein the first wavelength is 532 nm and the second wavelength is 785 nm.

18. The method according to claim 10, wherein the well depth is 6 mm.

19. The method according to claim 10, wherein the well diameter is 7 mm.

20. The method of claim 10, wherein the well minimizes masking of spectral readings, thereby improving sensitivity and discrimination between cancer and non-cancer spectra.

21. A method of determining an indication of the presence of colorectal cancer in a subject, comprising:
placing an unmodified liquid blood, serum, or plasma sample obtained from the subject in a Raman spectrometer well, wherein said well is metal and substantially circular having a diameter between 6 mm and 8 mm and a depth between 5 mm and 7 mm;
performing laser Raman spectroscopy on the unmodified liquid blood, serum, or plasma sample obtained from the subject in order to obtain at least one output spectrum;

comparing the output spectrum to a control dataset comprising a plurality of known output spectra, where the plurality of known output spectra are derived from the unmodified liquid blood, serum, or plasma samples of a plurality of first subjects having colorectal cancer and plurality of second subjects not having colorectal cancer;

identifying the presence of colorectal cancer in the subject from the comparing; and administering a follow-up treatment to the subject, wherein the follow-up treatment comprises one or more of a colonoscopy, colectomy, or chemotherapy.

22. The method of claim 21, wherein the well minimizes masking of spectral readings, thereby improving sensitivity and discrimination between cancer and non-cancer spectra.

* * * * *